United States Patent [19]

Mitchell

[11] 4,422,975

[45] Dec. 27, 1983

[54] ORGANIC SALT COMPOSITIONS IN EXTRACTION PROCESSES

[75] Inventor: Howard L. Mitchell, Baton Rouge, La.

[73] Assignee: Exxon Research and Engineering Co., Florham Park, N.J.

[21] Appl. No.: 289,323

[22] Filed: Aug. 3, 1981

[51] Int. Cl.$^3$ .............................................. C07F 5/06
[52] U.S. Cl. ........................... 260/448 AD; 260/429.3; 260/429.5; 260/448 C; 568/2; 585/827; 585/830; 585/831; 502/401
[58] Field of Search ............ 260/448 C, 429.3, 429.5, 260/448 AD, 448 A; 252/431 N, 431 P, 431 R; 568/2

[56] References Cited

U.S. PATENT DOCUMENTS

| | | | |
|---|---|---|---|
| 3,929,849 | 12/1975 | Oswald | 260/448 C |
| 3,954,821 | 5/1976 | Herskovitz et al. | 260/429 R |
| 3,987,009 | 10/1976 | Young | 252/431 P |
| 4,008,281 | 2/1977 | Knowles et al. | 260/429 R X |
| 4,013,700 | 3/1977 | Cawse | 260/449 R |
| 4,053,493 | 10/1977 | Oswald | 260/448 C |
| 4,105,578 | 8/1978 | Finlayson et al. | 260/448 C |
| 4,136,103 | 1/1979 | Oswald | 260/448 C |
| 4,179,403 | 12/1979 | Kim et al. | 252/431 P X |
| 4,183,825 | 1/1980 | Carlock | 252/431 P X |
| 4,208,218 | 6/1980 | Finlayson | 260/448 C |
| 4,269,762 | 5/1981 | Thomas | 568/2 |
| 4,287,166 | 9/1981 | Dwyer et al. | 252/431 P X |
| 4,294,989 | 10/1981 | Knowles et al. | 260/429 R X |
| 4,302,401 | 11/1981 | Oswald | 260/448 C |

OTHER PUBLICATIONS

Inorganic Chemistry, vol. 10, pp. 2840-2847 (1979) to W. H. Quayle and T. J. Pinnavaia.

Quayle et al, Inorganic Chemistry, Vol. 10, pp. 2840-2847 (1979)

*Primary Examiner*—Helen M. S. Sneed
*Attorney, Agent, or Firm*—Robert J. North

[57] ABSTRACT

Novel solid salt compositions are described containing, for example, tetraaryl- and triarylaralkyl-phosphonium and arsonium cations and tetraaryl- and tetraaryloxy-boranates and aluminates and polyanionic metal oxide surfaces, for example, as anions. The salts are useful for extracting aromatics and olefins from paraffinic hydrocarbon and aqueous liquid feedstreams, and from vapor and gas feedstreams by absorption.

20 Claims, No Drawings

ORGANIC SALT COMPOSITIONS IN EXTRACTION PROCESSES

BACKGROUND OF THE INVENTION

This invention relates to a process for the extraction of aromatics from process gas streams containing various organic components such as tail gas streams from catalytic cracking, the hydrogen stream from catalytic reforming of naphthas, exit gas streams from petrochemical processing reactors, and the like. More particularly, this invention is concerned with the use of organic salts, in particular, quaternary organic ammonium, phosphonium, and arsonium salts with inorganic and organic anions, including halides and pseudohalides, as well as organic quaternary boranates, borates and aluminates as absorption agents, both alone and supported, for the organic or some of the organic components in the process gas streams, even at quite high temperatures. Because of the non-volatility of these materials as salts and their low solubility in hydrocarbon or polar liquids, these salts are also usable as selective sorbants for extraction of aromatics and other polar organics at lower temperatures when contacted with liquid process streams or waste water streams at lower temperatures. Such salts show the exceptionally low volatilities of salts, essentially nil, thus allowing their contact with large amounts of gases flowing at high rates without significant losses and facilitating the recovery of extractate or absorbate. The polarity of the materials as salts and their very large sizes and the essentially spherical shapes of the component ions make the materials essentially insoluble and such melting, as may take place, only seems to allow the materials to become tacky or semi-solid under operable absorption conditions. The materials have the exceptional thermal stability for the high temperature conditions and do not steam-distill as do more conventional organic absorbants.

In certain instances, it is desirable to remove organics to prevent pollution of the air and water. In other instances, it is desirable to selectively remove and recover aromatics or olefins from gas streams which are to be used as fuel for burning and which are too dilute for recovery by conventional means, and thus, the aromatics or olefins are wasted. In other instances, the hydrocarbon gases in the hydrogen off-gas from catalytic naphtha reforming are undesirable impurities and present absorption methods are less than entirely efficient. Furthermore, there are petrochemical gas streams where olefins are present in gas streams and it is desirable for selective recovery for recycle, but they are present in such dilute state that present methods are relatively rarely used and considerable quantities are lost to uses as fuel. Yet further liquid process feed streams are instances where the presence of trace aromatics or olefins can poison process catalysts, as in paraffin isomerization, and removal of the trace polar contaminants is most desirable and necessary, but present absorption and extraction methods are less than adequate and the usual feed preparation involves an expensive exhaustive hydrogenation step.

SUMMARY OF THE INVENTION

By contrast, the solid organic salts of the present invention have the unique physical and chemical properties which allow the above problems to be solved by simple and straightforward selective absorption of polar organics or organics in general, from liquid hydrocarbon and water streams or from dilute gas streams at low or high temperatures, even high temperatures where conventional organics are of little value as absorbants. The organic salts of this invention are easily synthesized from readily available starting materials and have very high thermal and chemical stability. They can be readily separated from extractate materials by steam stripping or similar such procedures and the extractate then recovered in a more concentrated form, relative to the original feedstream.

According to this invention, there is provided a composition of matter, being a solid salt, of the formula:

[C] [A]

wherein [C] is a monovalent or divalent cation selected from the group consisting of the formulae:

$[R_4Q]$ $[R_3R'Q]$ $[R_3Q\text{-}L\text{-}QR_3]$, and

[A] is a monovalent or divalent anion or a polyanionic metal oxide selected from the group consisting of the formulae:

$[R''_4M]$

[AS]

$[R''_3M\text{-}L'\text{-}MR''_3]$ wherein Q is independently N, P or As;

R is independently selected from the group consisting of phenyl, naphthyl, biphenylyl, and their monochloro and monomethyl derivatives;

R' is selected from the group consisting of benzyl, naphthylmethyl, and their monochloro and monomethyl derivatives; linear and branched $C_6$–$C_{12}$ alkyl; cyclopentyl, cyclohexyl, adamantyl, bicyclooctyl, their monomethyl, dimethyl, partially fluorinated and partially chlorinated derivatives;

R'' is independently selected from the group consisting of phenyl, naphthyl, phenoxy, naphthoxy, and their methyl, polymethyl, chloro, polychloro, fluoro and polyfluoro derivatives;

L is $-CH_2-(p-C_6H_4)-CH_2-$;

L' is $p-C_6H_4$;

M is B or Al;

[AS] is a solid polyanionic metal oxide in which the metal is independently selected from the group consisting of Al, Si, Ti, Zr, Th, Hf, W, B and mixtures thereof; and wherein the number of cations and anions are sufficient to render the salt electrically neutral.

Preferred embodiments of the cation are where Q is P, [C] is $[R_4Q]$, $[R_4P]$ and $Ph_4P$.

Preferred embodiments of the anion [A] are $[R''_4M]$, wherein M is B or Al, and wherein at least one R'' is aryloxy, and preferably all four R'' radicals are aryloxy, or [AS], wherein the metal of the metal oxide of the [AS] salt is Al or Si. Most preferably, the metal of the metal oxide of [AS] is Al.

Where the anion is other than [AS], preferably the composition contains one cation and one anion. Where the anion is [AS], the composition is a metal oxide having the defined cations absorbed onto the surface producing an electrically neutral composition.

Further provided is a process for extracting aromatic and olefinic hydrocarbons and organic hydrocarbons from mixed liquid or gaseous feedstreams, containing paraffins comprising contacting said feedstreams with the compositions defined and described above at a temperature in the range of about 20°–500° C.

Also provided is a composition, being a solid salt, of the formula:

[C] [A]

wherein [C] is a monovalent or divalent cation of the formula:

[R$_4$Q]

wherein Q is P or As;

R is an aryl radical independently selected from the group consisting of phenyl, naphthyl, monochloro and monomethyl derivatives thereof; and

[A] is an anion independently selected from the group consisting of the formulae:

[R"$_4$M]

[R$_3$"M-L'-MR"$_3$]

[AS], wherein R" is independently selected from the group consisting of phenyl, naphthyl, phenoxy, naphthoxy, and their methyl, polymethyl, chloro, polychloro, fluoro and polyfluoro derivatives:
M is B or Al;
L' is p-C$_6$H$_4$;
[AS] is a solid polyanionic metal oxide in which the metal is independently selected from the group consisting of Al, Si, Ti, Zr, Hf, Th, W and B, and mixtures thereof, wherein the number of cations and anions is sufficient to render the salt electrically neutral.

Preferred is wherein Q is P, [A] is [AS], and the metal of metal oxide is Al. Also preferred is the composition in which [A] is [R"$_4$M] M is Al, and all four R" radicals are phenoxy.

Furthermore, there is provided a process for selectively absorbing olefins and aromatics from gaseous feedstreams containing paraffins comprising contacting said feedstreams with the above-described composition, in the immediately preceding paragraph, at a temperature in the range of 250°–500° C.

DESCRIPTION OF THE INVENTION

Representative examples of the quaternary and other solid anions useful in the highest temperature absorptions and extractions include tetraphenylboranate [BPh$_4$], tetraphenylaluminate [AlPh$_4$], tetraphenoxyaluminate [(Ph-O)$_4$Al], tetraphenoxyboranate [(Ph-O)$_4$B], phenoxytriphenylboranate [(Ph-O-)BPh$_3$], phenoxytriphenylaluminate [(Ph-O-)AlPh$_3$], pentafluorophenyltriphenylboranate [(C$_6$F$_5$)BPh$_3$], pentachlorophenyltriphenylaluminate [(C$_6$Cl$_5$)AlPh$_3$], p-methylphenyltriphenylboranate [p-CH$_3$(C$_6$H$_4$)BPh$_3$], p-bis(triphenylboranate)benzene, and high surface area metal oxides [AS] including gamma alumina [gamma-Al$_2$O$_3$], silica [SiO$_2$], zirconia on alumina [gamma-Al$_2$O$_3$-ZrO$_2$], aluminosilicates [Al$_2$O$_3$-SiO$_2$], titania-silica [TiO$_2$-SiO$_2$], and the like.

Novel quaternary anions among those above include those with phenoxy and substituted phenoxy R" radicals, in particular the anions [A] of formula [R"$_4$M] wherein R" is an aryl or aryloxy radical independently selected from the group consisting of phenyl, naphthyl, phenoxy, naphthoxy, and their methyl, polymethyl, chloro, polychloro, fluoro and polyfluoro derivatives; M is B or Al; and preferably where at least one R" is chosen from among those with oxy linkages to the heteroatom M. Such novel quaternary anions are preferred because the aryloxy functionalities are particularly inexpensive to produce relative to the aryl functionalities, although their stabilities are comparable. Most preferred is where all four R" radicals are aryloxy.

Preparations of the novel aryloxy-substituted anions [A] are by quite modern techniques, a fact which again emphasizes their unexpected nature since they were of a group not previously considered to be synthesizeable. The key aspects to their preparations involve the modern use of polar non-hydroxylic solvents and the necessity to avoid even traces of water or protonated oxygens in the preparation system. The following examples use the phenoxide R" radical as the example giving an illustrative example of the best mode of carrying out this preparative invention, as contemplated by us, and should not be construed as being a limitation on the scope or spirit of the instant invention. The equation below describes the overall reaction of the two readily available starting materials.

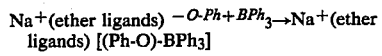
Na$^+$(ether ligands) $-^{O\text{-}Ph+BPh_3}\rightarrow$Na$^+$(ether ligands) [(Ph-O)-BPh$_3$]

The sodium phenoxide and triphenylborane, sometimes called triphenylboron were combined in one-to-one molecular ratio in ether solution at the reflux temperature of the ether, with both materials being slowly brought together as dilute solutions from separate Soxhlet extractors, the salt then crystallizing from the solution as formed. The preparation experiment was done both with tetrahydrofuran and with dimethylether as solvent, the latter appearing to function best. The solvents and starting materials were exceptionally well dried and deprotonated by standard but exhaustive techniques, e.g., distillation of solvents from LiAlH$_4$ under nitrogen, flame drying glassware under dried N$_2$ flow, vacuum system sublimation of Ph$_3$B in the presence of tert-butyllithium, vacuum transpiration of excess PhOH and H$_2$O from the NaOPh, and drying and dehydrogenation of the inert N$_2$ under which the reaction was run by passing it through a triethylaluminum-treated gamma-Al$_2$O$_3$ bed in a quartz tube furnace at 120° C. Workup of the preparations is not sensitive and simply involves separation of the crystalline material, which retained considerable ether from the solvent as ligands for the Na$^+$ ions. The retained solvent was inconsequential for the subsequent uses in the preparations of the salts which contain the organic cations as well as organic anions. Other preparations involved similar procedures on other available starting materials such as triphenoxyborate (PhO)$_3$B, triphenoxyaluminate (PhO)$_3$Al, triphenylaluminum Ph$_3$Al, etc. Elemental analyses were utilized as proofs of structure and were required to fit those theoretically necessary within experimental error.

The remaining organic anions are prepared by very similar but complementary means by contacting in one to one molecular ratio arylithium compounds in inert solution under inert atmosphere conditions with the appropriate tertiary boron or aluminum material with the product crystallizing out, filtering to remove solvent, and then appropriate drying. The equation of the example below shows the preparation of lithium p-methylphenyltriphenylboranate in 1:1 benzene-THF as solvent.

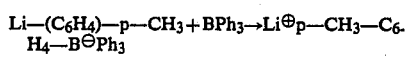

Li—(C$_6$H$_4$)—p—CH$_3$+BPh$_3$→Li$^\oplus$p—CH$_3$—C$_6$H$_4$—B$^\ominus$Ph$_3$ The same sort of inert atmosphere and apparatus and solvent drying precautions are taken in this group of anion preparations as in the preparation of the abovedescribed novel quaternary organic anions except in the product workup where the materials, aside from simple absorption of water, are not air sensitive.

Representative examples of the cations useful in the highest temperature absorptions and extractions fit the formula [R$_4$Q] and include tetraphenylphosphonium, tetraphenylarsonium, p-methylphenyltriphenylphosphonium, p-chlorophenyltriphenylphosphonium, p-methylphenyltriphenylarsonium, p-chlorophenyltriphenylarsonium and 1-naphthyltriphenylarsonium ions, the group of highest thermal stability. This highest thermal stability is present because only aromatic carbons are attached to the heteroatom Q, with the aromatic π-electron clouds stabilizing the ⊕ charge.

Representative examples of the cations useful in the high temperature absorptions and extractions, but not limited to the highest temperature range, include tetraphenylphosphonium, tetraphenylarsonium, p-methylphenyltriphenylarsonium, p-chlorophenyltriphenylarsonium, 1-naphthyltriphenylarsonium, p-methylphenyltriphenylphosphonium, p-chlorophenyltriphenylphosphonium, benzyltriphenylammonium, benzyltriphenylphosphonium, benzyltriphenylarsonium, tetrabenzylammonium, p-methylbenzyltribenzylammonium, p-methylbenzyltriphenylphosphonium, p-chlorobenzyltriphenylphosphonium, p-methylbenzyltriphenylarsonium, p-chlorobenzyltriphenylarsonium, α,α-bis(triphenylphosphonium)-p-xylene, adamantyltriphenylphosphonium, adamantyltriphenylarsonium, 2-ethylhexyltriphenylphosphonium, and 3-chloro-4-fluorocyclopentyltriphenylphosphonium ions, the group of relatively high thermal stability. The thermal and chemical stability is quite high due to three aromatic R radicals attached to the heteroatom Q, but the aliphatic fourth R' is a weaker bond to the Q atom.

By the term "partially fluorinated" and "partially chlorinated" is meant less than the total number of fluoro and chloro groups to achieve the perhalogenated structure.

The following non-limiting examples are illustrative of the best mode of preparation of the solid organic salts. The quaternary organic cations are prepared by means of the reaction of a tertiary amine, phosphine, or arsine with an alkyl or aryl halide, sulfate, phosphate, sulfonate, or other such reactive compound. Fluoride is an inappropriate halide, and the heavier the halide, the better, although more expensive. Toluene-, benzene-, or methanesulfonates and sulfates are quite good. The materials in one-to-one molecular ratio are heated together and added as in the following example showing the preparation of p-methylphenyltriphenylphosphonium bromide by heating at 200° C. for four weeks without solvent and another four weeks after the addition of two volumes of diphenylether as solvent in order to complete the reaction in conventional glass apparatus under a nitrogen atmosphere. The product crystallized out upon cooling and the solvent removed from the crystals by filtration and drying in a N$_2$ flow at elevated temperatures (~100° C.).

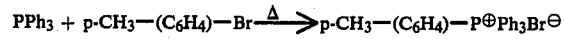

PPh$_3$ + p-CH$_3$—(C$_6$H$_4$)—Br $\xrightarrow{\Delta}$ p-CH$_3$—(C$_6$H$_4$)—P$^\oplus$Ph$_3$Br$^\ominus$ The general reaction for preparation of the combination salts with quaternary organic cations and quaternary organic anions is novel, albeit somewhat difficult to accomplish without occluding as impurities the relatively insoluble starting material salts of the types described above. The preparation of the combination salts is effected by contacting in one-to-one molecular ratio the quaternary organic cations and anions as their, for instance, halide and alkali metal salts respectively, in dilute dichloromethane solution, the salts being slowly introduced by simultaneous Soxhlet extraction of the thoroughly dried precursor salts in conventional apparatus. The product salt crystallizes out as a mixture of separate substances which, after filtration to remove solvent, then is susceptible to facile separation by a simple water wash to remove the inorganic salt before final drying of the purified organic salt. The example of the preparation of p-methylphenyltriphenylphosphonium p-methylphenyltriphenylboranate (also called p-tolyltriphenylphosphonium p-tolyltriphenylboranate) is shown in the following equation:

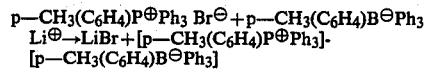

p—CH$_3$(C$_6$H$_4$)P$^\oplus$Ph$_3$ Br$^\ominus$+p—CH$_3$(C$_6$H$_4$)B$^\ominus$Ph$_3$ Li$^\oplus$→LiBr+[p—CH$_3$(C$_6$H$_4$)P$^\oplus$Ph$_3$]·[p—CH$_3$(C$_6$H$_4$)B$^\ominus$Ph$_3$]

Such large combination salts of large quaternary organic cations and large quaternary organic anions are unique and previously unknown, even though some of the component parts were known and used for other purposes.

The preparation of the solid quaternary organic salts of the general formulae [R$_4$Q][AS], [R$_3$R'Q][AS] and [R$_3$Q-L-QR$_3$][AS] all fall into the same general procedure, a variation of the above procedure for the preparation of the similar salts with quaternary organic anions. These salt materials are prepared from preferably, but not limited to, high surface area polyanionic metal oxide supports, preferably above 100 m$^2$/g, and most preferably above 150 m$^2$/g, by deposition of the quaternary organic cation as its simple salt, e.g., halide, sulfonate, and the like, onto it from dilute solution. The actual procedure for the example below is illustrated:

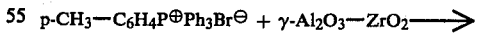

p-CH$_3$—C$_6$H$_4$P$^\oplus$Ph$_3$Br$^\ominus$ + γ-Al$_2$O$_3$—ZrO$_2$ ⟶

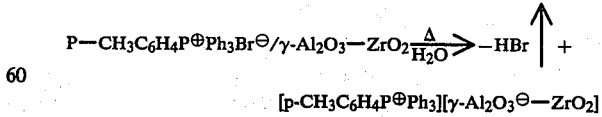

P—CH$_3$C$_6$H$_4$P$^\oplus$Ph$_3$Br$^\ominus$/γ-Al$_2$O$_3$—ZrO$_2$ $\xrightarrow[H_2O]{\Delta}$ —HBr ↑ +

[p-CH$_3$C$_6$H$_4$P$^\oplus$Ph$_3$][γ-Al$_2$O$_3$$^\ominus$—ZrO$_2$]

The dried p-tolyltriphenylphosphonium bromide is deposited from dilute solution by Soxhlet extraction in dichloromethane (methylene chloride) onto the prepared metal oxide support. The support was prepared by impregnating by standard incipient wetness impregnation techniques, 100 g of a γ-Al$_2$O$_3$ catalyst support of 203 m²/g surface area and no measurable sodium or alkali metal content, with 7.7 mmoles of zirconium n-propoxide in n-propanol. This material was dried and then steamed at 150° C. for 16 hours and then dried in a flow of dry air at the same temperature for 4 hours before the deposition of the quaternary organic salt. The quantity of 10 mmoles of the phosphonium bromide was deposited by the Soxhlet extraction with the zirconia-alumina within the pot of refluxing dichloromethane solvent. After separation of the solvent and drying, the solid material was steamed for 16 hours at 200° C. and then for 8 hours at 400° C. to eliminate any remaining HBr from the sorbant.

More particular comments pertaining to the general compositional formula defined in the Summary of The Invention are that preferred embodiments of the composition include where Q is phosphorous and M is boron or aluminum and particularly preferred is aluminum.

Preferred is wherein the anion [A] is [AS] comprising a polyanionic metal oxide and wherein the metal in said [AS] is preferably Al or Si and most preferably Al.

The cation [C] preferably is [R₄Q] and wherein Q is P or As, and most preferably P. Particularly preferred as [C] is [R₄P] wherein R is aryl and most particularly Ph₄P.

Representative examples of compositions of the subject invention are tetraphenylphosphonium tetraphenylboranate, tetraphenylphosphonium p-tolyltriphenylboranate, tetraphenylphosphonium tetraphenoxyboranate, tetraphenylphosphonium phenoxytriphenylaluminate, tetraphenylphosphonium tetraphenoxyaluminate, tetraphenylphosphonium p-bis(triphenylboranate)benzene, tetraphenylphosphonium tetraphenylaluminate [Ph₄P][Ph₄Al], tetraphenylphosphonium pentafluorophenyltriphenylboranate, tetraphenylphosphonium tetrakis(pentachlorophenoxy)aluminate, tetraphenylphosphonium tetrakis(pentafluorophenoxy)boranate, tetraphenylphosphonium zirconia-aluminosilicate, tetraphenylphosphonium alumina (or aluminate), tetraphenylphosphonium aluminosilicate, tetraphenylphosphonium silicate, tetraphenylphosphonium aluminotitanate, tetraphenylphosphonium titania-alumina, tetraphenylphosphonium titania-aluminosilicate, tetraphenylphosphonium titania (or titanate), tetraphenylphosphonium boriaalumina, tetraphenylphosphonium zirconium-alumina, tetraphenylarsonium tetraphenylboranate, tetraphenylarsonium tetraphenylaluminate, tetraphenylarsonium tetraphenoxy aluminate, tetraphenylarsonium zirconia-alumina (or zirconia-aluminate), p-chlorophenyltriphenylphosphonium tetraphenylboranate, p-chlorophenyltriphenylphosphonium gamma aluminate, p-chlorophenyltriphenylphosphonium silicate, p-tolyltriphenylphosphonium tetraphenylboranate, p-tolyltriphenylphosphonium zirconia-alumina, 2-naphthyltriphenylarsonium tetraphenylboranate, p-biphenylyltriphenylphosphonium tetrakis(p-biphenylylaluminate), p-biphenylyltriphenylphosphonium p-trifluoromethylphenyltriphenylboranate, 6-methyl-2-naphthyltriphenylarsonium tungstia-alumina, tetrakis(p-biphenylyl)phosphonium thoria-alumina, tetrakis (p-biphenylyl)phosphonium hafnia-alumina, benzyltriphenylphosphonium tetraphenylboranate, benzyltriphenylphosphonium p-tolyltriphenylboranate, benzyltriphenylphosphonium phenoxytriphenylboranate, benzyltriphenylphosphonium tetraphenoxyboranate, benzyltriphenylphosphonium tetraphenylaluminate, benzyltriphenylphosphonium tetraphenoxyaluminate, benzyltriphenylphosphonium phenoxytriphenylaluminate, benzyltriphenylphosphonium p-bis(triphenylboranate)benzene, benzyltriphenylphosphonium tetrakis(pentachlorophenoxy)aluminate, benzyltriphenylphosphonium p-chlorophenyltriphenylboranate, benzyltriphenylphosphonium alumina, benzyltriphenylphosphonium titania, benzyltriphenylphosphonium silica, benzyltriphenylphosphonium aluminosilicate, benzyltriphenylphosphonium zirconia-aluminosilicate, benzyltriphenylphosphonium titaniaaluminosilicate, benzyltriphenylphosphonium boria-alumina, benzyltriphenylphosphonium titania-alumina, benzyltriphenylphosphonium zirconia-alumina, benzyltriphenylphosphonium aluminum oxyfluoride-alumina, benzyltriphenylarsonium tetraphenylboranate, benzyltriphenylarsonium tetraphenoxy aluminate, benzyltriphenylarsonium tetraphenoxyboranate, benzyltriphenylarsonium zirconia-alumina, benzyltriphenylammonium tetraphenylboranate, tetrabenzylammonium tetraphenylboranate, tetrabenzylammonium tetraphenoxyaluminate, tribenzyl-p-methylbenzylammonium tetraphenylboranate, p-methylbenzyltriphenylphosphonium tetraphenylboranate, p-methylbenzyltriphenylphosphonium p-tolyltriphenylboranate, p-methylbenzyltriphenylphosphonium zirconia-aluminosilicate, bis(triphenylphosphonium)p-xylylene tetraphenylboranate, p-chlorobenzyltriphenylphosphonium tetraphenylboranate, tetra-p-tolylphosphonium tetraphenylboranate, 2- L -ethylhexyltriphenylphosphonium tetraphenylboranate, 2-ethylhexyltriphenylphosphonium tetraphenoxyaluminate, 1-adamantyltriphenylphosphonium tetraphenylboranate, (p-tolyl)-p-benzyltriphenylphosphonium tetrakis(trichlorophenoxy) aluminate, and the like.

Particularly preferred examples are tetraphenylphosphonium tetraphenylboranate, tetraphenylphosphonium aluminosilicate, tetraphenylphosphonium tetraphenoxy aluminate, tetraphenylphosphonium zirconia-alumina, benzyltriphenylphosphonium tetraphenylboranate, benzyltriphenylphosphonium tetraphenoxyaluminate, benzyltriphenylphosphonium aluminosilicate, and benzyltriphenylphosphonium zirconia-alumina.

The subject compositions are solid salts, and by the term "solid" is meant that the salts are solid at ambient temperature and substantially solid at the temperatures of use, and as such, are not pumpable or pourable except as particles or particulates or slurries, e.g., fluidized solids; however, they may become somewhat tacky upon absorption of other organic materials, e.g., during use as absorption or extraction agents.

The unique compounds of the present invention are useful in two novel types of related processes. The more thermally stable materials are useful in high temperature absorption of organics or polar organics from hot gas phase feedstreams with subsequent recovery of absorbed organics by steam stripping and condensation. The group of compounds operable for these high temperature absorptions include those of formulae $[R_4Q][R''_4M]$, $[R_4Q]_2[R''_3M-L'-MR''_3]$, and $[R_4Q][AS]$. These materials are also useful for extraction and absorption from liquids at both the higher and lower temperatures when the process is operated at at least a pressure sufficient to maintain the feedstream as a liquid. The extraction may be done in fixed-bed, moving-bed, slurry, or other similar manner in equipment typical for contacting a liquid, vapor, or gas with solid absorbants or extractants. For best results, effectively, countercurrent contacting of the feed with the solid extractant in a batch system or continuous system is preferred, although these are not to be construed as constituting the limitations of the invention. Likewise, the absorption of organics, either selectively or nonselectively, can be effected in essentially similar fixed-bed, moving-bed, fluidized-bed, or raining solids processes in conventional equipment.

The low temperature solid salt extraction and absorption processes can be accomplished at temperatures from ambient (20° C.) up through about 400° C., preferably below 325° C., and most preferably below 250° C. The high temperature solid salt extraction and absorption processes can be accomplished at temperatures up to about 500° C., but preferably below about 450° C. Thus, the range of extraction processes is from 20°–500° C. In both high temperature and low temperature processes, the process must be conducted at a temperature below the decomposition temperature of the particular salt or salts in use for the extraction or the absorption. Generally, for selective aromatics extraction from liquid or gaseous feedstreams, the lowest possible temperatures, compatible with other upstream or downstream processes and the associated economics, should be utilized to obtain maximum selectivity and capacity of the solid salts due to the necessity of combating the volatility of the aromatic compounds at high temperatures. Likewise, the absorption of gaseous organics is most preferred at the lowest temperature compatible with surrounding processes due to the increasing selectivity and capacity at lower temperatures because of the necessity of combating the volatility of the low molecular weight molecules being absorbed.

The feedstreams operable in the processes are liquids, vapors or gases containing paraffins at temperatures in the range of about 20°–500° C.

A preferred process is for selectively absorbing olefins and aromatics from gaseous feedstreams containing paraffins comprising contacting said feedstreams with the subject composition described herein, wherein Q is P, [A] is [AS] and said metal of said metal oxide is Al and said temperature is in the range of 250°–500° C.

The quaternary organic salts of the present invention can be used as mixtures, however, it is quite preferred that they be used as a single or pure material. This preferred mode of use of the solid salts is in direct contrast with the related mode of use of the less aromatic liquid quaternary organic salts and their use as liquid solvents for extraction of aromatics from paraffinic hydrocarbons for which the preferred mode of use is as mixtures of the salts, either mixtures of cations or anions or both.

The operation of these solid organic salts as extractants or absorbants is considerably different than the liquid salt solvent systems, which function by way of mutual solubility of the aromatics and liquid salts, and also different from simple high surface area absorbants such as activated carbons, etc., which function by absorption onto a surface at active sites. The solid organic salts of the instant invention function by accepting guest molecules into the holes within the solid structure and between the ions which make up the salt. The ions have considerable potential and ability to move aside temporarily to allow the guest molecules to enter the lattice spaces. Such behavior is in contrast to the typical clathrate behavior wherein guest molecules can only be included into the host molecule crystal lattice during crystallization of the host substance. Because these quaternary organic salts of the present invention have the ability to move enough to allow "dissolution" or "inclusion" of the guest molecules readily into the solid structure, they are much more useful for extraction and absorption than the conventional clathrate separation materials and processes, and likewise, more useful than the less selective carbon absorptions and liquid solvent extractions.

The large ions of the solid combination quaternary organic salts of the present invention are roughly spherical in shape such that each pair of a cation and anion, a neutral pair, can be considered to be a pair of spheres, roughly approximating billiard ball models, and the set of such spheres in a solid crystal also approximating the stacking of billiard ball spheres. Such crystal latices have considerable spaces of particular volumes, shapes, and positions into which guest molecules can be put. The fact that these salts accept and release such guest molecules during the normal course of use is unique to their structure and provides for some additional unique uses and selectivities of extraction and absorption of organic molecules. Such sets or lattices of ions behave in some ways almost as if they were sieve-like. The organic cation salts of the present invention with the solid metal oxide surface anions then can be visualized as if they were a layer or several layers of the spherical cations covering the high surface area support-type anion, which might thus be approximated as a set of billiard ball type spheres sitting on a group of flat or nearly flat surfaces with the available spaces being, not only between the spheres, but also between the spheres and the flat surfaces.

A particularly unique property of the combination quaternary organic salts and also of the salts of quaternary organic cations with solid surface anions is their exceptionally modifiable nature, specifically synthesizeable into the ions during preparation. Parts of the ions can be changed, enlarged, extended, polarized, etc., simply by substituting R, R', R", L, and L' groups of different composition, shape, structure, etc. In such manner, the sizes and shapes of the lattice spaces, polarities, hardness or softness and thus interactability with $\pi$-electron clouds of guest molecules, and other such chemical and physical properties can be specifically tailored to the actual use and process intended for the salt.

Consequently, it is clear why the group of organic salts of the present invention function better as pure or neat materials rather than as mixtures, with any mixed salt impurities tending to decrease the selectivity and capacities by partially or wholly filling and eliminating some of the void spaces where guest molecules would locate during extraction or absorption.

The void spaces between and among the organic ions in the instant invention are tailored for the specific use by choice of radicals on the ions. Large chlorine substituents and methyl substituents on the aromatics of the R radicals increase overall size but can give either increased size or decreased size depending on the particular combinations. Chlorine substituents on R radicals are preferred for selective extraction or absorption of aromatics, olefins, or polar species, whereas the use of methyl group substituents on the R radicals is preferred for paraffinic or general organic absorption or extraction, e.g., methane absorption from $H_2$ streams. The presence of at least one non-hydrogen substituent in the R radical of an ion of the salt is preferred over the solely hydrogen substituted R group salts because of increased rates of absorption, extraction and removal of extractate or absorbate. Conversely, the use of solely hydrogen substituted R and R" radicals of the salts is preferred due to higher thermal and chemical stability and lower basic costs. The use of aluminum anions is preferred due to lower basic costs, but the use of boron anions is preferred due to generally better stability. Phosphonium cations are greatly preferred over those of As and N due to cost and stabilities and ease of manufacture, while salts of As are preferred over those of N due to stability. High temperature salts of nitrogen cations are generally not synthesizeable and operable in the present invention process.

The ease of separation of the extractant or adsorbate from the feed stream and then from the extractate are also very important characteristics that the salts should possess. This characteristic is extremely important when it is desired to reduce the concentration of aromatic hydrocarbons in the feedstreams to extremely low concentrations and to avoid any possible contamination of the feedstream with absorbant as in the preparation of feeds for paraffin isomerization. Conventional liquid solvents such as sulfolane, cannot be reduced to the aromatic-free state because of their volatility. By contrast, the instant solid organic salts have essentially zero volatility, and are readily freed of aromatics by stripping, steam distillation, etc., and they have essentially zero solubility in paraffinic solvents and feed streams. Complete recovery of aromatic extractate is possible and thus separation of solvent or chemical intermediate aromatics from aromatics-rich naphthas are thus also possible.

The phosphonium salts are most preferred because of thier thermal and chemical stability; arsonium salts are less preferred, but are preferred to the least stable ammonium salts. The same order of preference, N<As<P, is also the same order or preference on the basis of costs and ease of preparation. When R radicals of derivatives of naphthalene are used, only As and P are usable as the heteroatom of the cation and As is greatly preferred for steric reasons; the stability of the N cations is entirely unsuitable due to steric crowding. It has been found that the operable salts for the lower temperature extractions and absorptions contain R' hydrocarbon radicals in the size range of $C_5$ to $C_{12}$, with branched and cyclic species most preferred.

Only quaternary organic ions, either cations or anions, are suitable for use in the extraction and absorption processes described herein. Other organic anions are generally too unstable thermally and chemically. Likewise, tertiary, secondary, and primary organic cations and anions are entirely too reactive and unstable to be operable in the described process.

The process feedstream in the process should be clean and have reasonably low molecular weight to avoid contamination of the salts with intractable polymers. Even traces of high molecular weight materials in the feedstream are to be avoided.

The temperature at which the high temperature extractions and absorptions can be conducted is in the range of 20°–500° C., but preferably should be minimized. However, certain types of processes, for example, absorption of aromatic hydrocarbons from gas streams, are best run at higher temperatures in order to obtain adequate rates of absorption. Consequently, it is preferred that high temperature absorption be effected at about 250° C. or higher and most preferably at about 325° C. or higher when rates are taken into account so that contact times can be minimized.

The compositions of the instant invention, particularly the class of alkyltriarylphosphonium salts, are also capable of removing aromatics and even aliphatic hydrocarbons from waste water streams.

Anion surface [AS] is less preferred than the organic anion due to lower selectivity of extraction toward aromatics relative to paraffinics, but more preferred due to economy of manufacture and materials cost and capabilities in process design.

The following non-limiting examples of the extraction and absorption processes are illustrative of the best modes of the invention process and are illustrative of both low and high temperature absorption and low temperature extraction. The examples should not be construed as being limitations on the scope and spirit of the instant invention.

EXAMPLE 1

High Temperature Absorption

A powder sample of 100 g. of tetraphenylphosphonium tetraphenylboranate was fluidized in a quartz tube furnace at 425° C. in a stream of a gas mixture of $N_2:CO_2:CO:H_2:C_2H_4$ of ratio 6:2:1:1:0.001 at ambient pressure, 755 torr, for the time necessary for 1000 volumes of the gas flow past the fluidized bed. The gas was then switched to $H_2O$ vapor at the same temperature and ethylene recovered by condensation and measurement by GC and mass spectrometer amounted to 93% of the calculated theoretical amount.

EXAMPLE 2

High Temperature Absorption

A powder sample (60–150 mesh) of 100 g of p-tolyltriphenylphosphonium γ-aluminozirconate of BET surface area of 142 $m^2/g$ was fluidized as above but in which the gas stream contained additional methane in an amount equal to that of the ethylene. The amounts of ethylene and methane recovered were equal to 91% and 24%, respectively.

EXAMPLE 3

Low Temperature Absorption

A 100 g sample of 14/35 mesh sorbant p-chlorophenylphosphonium γ-aluminate of BET surface area of 168 $m^2/g$ was contacted in a fixed bed in a quartz tube furnace with a down-flow gas stream containing $N_2:C_6H_6:n-C_7H_{16}$ in ratio of 8:1:1 at 250° C. with 100 volumes of gas with the workup as above. The amounts of benzene and heptane recovered were equal to 85% and 11%, respectively, of the calculated theoretical amounts.

EXAMPLE 4

Low Temperature Absorption

A 100 g sample of 14/35 mesh sorbant p-methylbenzyltriphenylphosphonium γ-aluminosilicatezirconate of 328 $m^2/g$ BET surface area was contacted with a gaseous feedstream as above in a fixed bed process at 225° C. with 100 volumes of $H_2$ and $CH_4$ in a volume ratio of 19:1. Workup as above, gave recovery of 74% of the calculated theoretical amount of methane.

EXAMPLE 5

Low Temperature Extraction

A 100 g sample of powdered tetraphenylphosphonium tetrakis(pentachlorophenyl)aluminate was slurried with 500 ml. of a liquid feed of benzene and heptane in 1:99 volume ratio at 300° C. at 1500 psig $N_2$ pressure, more than sufficient to maintain the feed as a liquid, and after stirring for 1 hour, the liquid decanted off. Steam stripping of the solids, still maintained at the same temperature allowed recovery of 88% of the benzene theoretically possible, as calculated on the basis of that in the original feed.

EXAMPLE 6

Low Temperature Absorption (Extraction)

100 g. of powdered benzyltriphenylphosphonium tetraphenoxyaluminate were slurried at 35° C. for 2 hours in 5 liters of water containing 650 parts per million benzene and 50 parts per million n-heptane. After separation and workup by $N_2$ stripping of the solids with dry ice condensation and measurement, as described above, 98% of benzene and 99% of n-heptane were recovered as having been extracted or absorbed from the aqueous solution, calculated on the basis of that originally present.

What is claimed is:

1. A composition of matter, being a solid salt, of the formula:

[C] [A]

wherein [C] is a monovalent or divalent cation selected from the group consisting of the formulae:

[$R_4Q$]

[$R_3R'Q$]

[$R_3Q$-L-$QR_3$], and

[A] is a monovalent or divalent anion or a solid polyanionic metal oxide selected from the group consisting of the formulae:

[$R''_4M$]

[AS]

[$R''_3M$-L'-$MR''_3$]

wherein
Q is independently N, P or As;
R is independently selected from the group consisting of phenyl, naphthyl, biphenylyl, and their monochloro and monomethyl derivatives;
R' is independently selected from the group consisting of benzyl, naphthylmethyl, and their monochloro and monomethyl derivatives; linear and branched $C_6$-$C_{12}$ alkyl; cyclopentyl, cyclohexyl, adamantyl, bicyclooctyl, their monomethyl, dimethyl, partially fluorinated and partially chlorinated derivatives;
R" is independently selected from the group consisting of phenyl, naphthyl, phenoxy, naphthoxy, and their methyl, polymethyl, chloro, polychloro, fluoro and polyfluoro derivatives;
L is —$CH_2$(p—$C_6H_4$)$CH_2$—;
L' is p-$C_6H_4$;
M is B or Al;
[AS] comprises a solid polyanionic metal oxide in which the metal is independently selected from the group consisting of Al, Si, Ti, Zr, Th, Hf, W, B and mixtures thereof; and wherein the number of cations and anions are sufficient to render the salt electrically neutral.

2. The composition of claim 1 wherein Q is phosphorus.

3. The composition of claim 1 wherein M is boron.

4. The composition of claim 1 wherein M is aluminum.

5. The composition of claim 1 wherein the anion [A] is [AS].

6. The composition of claim 1 wherein the metal of the metal oxide of the [AS] is Al.

7. The composition of claim 1 wherein the metal in [AS] is Al or Si.

8. The composition of claim 1 wherein [C] is [$R_4Q$].

9. The composition of claim 8 wherein [C] is [$R_4P$].

10. The composition of claim 1 wherein at least one R" in [$R''_4M$] is phenoxy, naphthoxy, and their methyl, polymethyl, chloro, polychloro, fluoro and polyfluoro derivatives.

11. The composition of claim 10 wherein all 4 R" radicals in [$R''_4M$] are selected from phenoxy, naphthoxy, and their methyl, polymethyl, chloro, polychloro, fluoro, and polyfluoro derivatives.

12. The composition of claim 1 wherein [C] is $Ph_4P$.

13. A composition of matter, being a solid salt, of the formula:

[C] [A], wherein [C] is a monovalent or divalent cation of the formula:

[$R_4Q$]

wherein
Q is P or As;
R is an aryl radical independently selected from the group consisting of phenyl, naphthyl, monochloro and monomethyl derivatives thereof; and
[A] is an anion independently selected from the group consisting of the formula:

[$R''_4M$]

[$R''_3M$-L'-$MR''_3$]

[AS], wherein
R" is independently selected from the group consisting of phenyl, naphthyl, phenoxy, naphthoxy, and their methyl, polymethyl, chloro, polychloro, fluoro, polyfluoro derivatives;
M is B or Al;
L' is p-$C_6H_4$;
[AS] comprises a solid polyanionic metal oxide in which the metal is independently selected from the group consisting of Al, Si, Ti, Zr, Hf, Th, W and B, and mixtures thereof, wherein the number of cations and anions is sufficient to render the salt electrically neutral.

14. The composition of claim 13 wherein Q is P.

15. The composition, tetraphenylphosphonium tetraphenyl boronate.

16. The composition, tetraphenylphosphonium aluminosilicate.

17. The composition, tetraphenylphosphonium tetraphenoxyaluminate.

18. The composition, benzyltriphenylphosphonium tetraphenylboranate.

19. The composition, benzyltriphenylphosphonium tetraphenoxyaluminate.

20. The composition, benzyltriphenylphosphonium aluminosilicate.

* * * * *